US010105482B1

(12) United States Patent
Holland

(10) Patent No.: US 10,105,482 B1
(45) Date of Patent: Oct. 23, 2018

(54) ENVELOPING ASSEMBLY AND METHOD FOR STERILIZED AND STATIC RESISTANT ORDERING OF MEDICAL WIRES AND TUBES

(71) Applicant: Laina M. Holland, Klamath Falls, OR (US)

(72) Inventor: Laina M. Holland, Klamath Falls, OR (US)

( * ) Notice: Subject to any disclaimer, the term of this patent is extended or adjusted under 35 U.S.C. 154(b) by 0 days.

(21) Appl. No.: 15/385,979

(22) Filed: Dec. 21, 2016

Related U.S. Application Data

(60) Provisional application No. 62/415,972, filed on Nov. 1, 2016.

(51) Int. Cl.

| | |
|---|---|
| ***A61M 5/32*** | (2006.01) |
| ***A61M 5/14*** | (2006.01) |
| ***F16L 3/137*** | (2006.01) |
| ***F16L 3/12*** | (2006.01) |
| ***F16L 3/233*** | (2006.01) |
| ***F16B 1/00*** | (2006.01) |
| ***A61G 7/05*** | (2006.01) |
| ***A61M 39/08*** | (2006.01) |

(52) U.S. Cl.

CPC ......... *A61M 5/1418* (2013.01); *A61G 7/0503* (2013.01); *A61M 39/08* (2013.01); *F16B 1/00* (2013.01); *F16L 3/1218* (2013.01); *F16L 3/137* (2013.01); *F16L 3/233* (2013.01); *F16B 2001/0028* (2013.01)

(58) Field of Classification Search

CPC ...... A61M 25/02; A61M 5/1418; A61B 46/23

USPC ......................... 604/174, 179, 180; 248/68.1

See application file for complete search history.

(56) References Cited

U.S. PATENT DOCUMENTS

| | | | | |
|---|---|---|---|---|
| 3,721,234 | A * | 3/1973 | Hadtke | A61B 46/00 128/852 |
| 4,074,397 | A | 2/1978 | Rosin | |
| 4,336,806 | A | 6/1982 | Eldridge, Jr. | |
| 4,639,980 | A | 2/1987 | Peterson | |
| 4,640,032 | A | 2/1987 | Lewis | |
| 4,664,103 | A | 5/1987 | Martin et al. | |
| 5,010,899 | A | 4/1991 | Thompson | |
| 5,037,397 | A * | 8/1991 | Kalt | A61M 25/02 604/174 |
| 5,082,111 | A | 1/1992 | Corbitt, Jr. et al. | |
| 5,464,025 | A | 11/1995 | Charles et al. | |

(Continued)

*Primary Examiner* — Todd M Epps
(74) *Attorney, Agent, or Firm* — Jerry Haynes Law

(57) ABSTRACT

An enveloping assembly and method for sterilized and static resistant ordering of medical wiring and tubes holds elongated electrical and tubular members for ordering, to prevent the elongated members from tangling or falling into a disorganized arrangement, especially near a medical procedure. The assembly comprises an outer panel defined by a flexible, sterilized fabric. An inner panel is disposed coplanar to the outer panel, lying within the edges of the outer panel. The inner panel is flexible and static charge resistant. The inner panel enables enveloping of the elongated members while preventing static discharge. The inner panel envelopes the elongated members by moving opposing edges of the inner panel to form a unitary sleeve, wherein the outer panel can envelope the unitary sleeve to protect the assembly from contamination. A fastener joins with the outer panel to fasten the unitary sleeve closed and detachably attach to a mounting surface.

17 Claims, 5 Drawing Sheets

(56) References Cited

U.S. PATENT DOCUMENTS

| | | | | |
|---|---|---|---|---|
| 5,535,787 | A | 7/1996 | Howell | |
| 5,624,403 | A | 4/1997 | Jaquith | |
| 5,709,665 | A | 1/1998 | Vergano et al. | |
| 5,836,453 | A | 11/1998 | Herrera | |
| 6,315,759 | B1 | 11/2001 | Peterson | |
| 7,077,272 | B2 * | 7/2006 | Shimada | A01K 63/04 210/288 |
| 8,366,058 | B2 | 2/2013 | Tiedemann, Sr. | |
| 9,522,001 | B2 * | 12/2016 | Bui | A61B 50/33 |
| 2003/0232163 | A1 | 12/2003 | Graham et al. | |
| 2015/0297295 | A1 | 10/2015 | Moe et al. | |

* cited by examiner

ENVELOPING ASSEMBLY AND METHOD FOR STERILIZED AND STATIC RESISTANT ORDERING OF MEDICAL WIRES AND TUBES

CROSS-REFERENCES TO RELATED APPLICATIONS

This application claims priority from U.S. Provisional Application Ser. No. 62/415,972, entitled "Enveloping Assembly and Method for Sterilized and Static Resistant Ordering of Medical Wires and Tubes", filed on Nov. 1, 2016, which application is hereby incorporated herein by reference in its entirety.

FIELD OF THE INVENTION

The present invention relates generally to an enveloping assembly and method for ordering of medical wiring and tubes. More so, the present invention relates to an enveloping assembly and method for sterilized and electrostatic resistant ordering of medical wiring and tubes that organizes electrical wires, cords, and tubes.

BACKGROUND OF THE INVENTION

During the course of hospitalization patients often require the use of support equipment to aid in their recovery. For example, during a surgical procedure, it is frequently desirable to have a system for holding elongated surgical equipment such as vacuum tubes, other tubing, wires, cords, sponges, clamps, suction tips and ring instruments in position close to a patient. The tubing which connects the patient to the equipment, such as oxygen, anesthesia, intravenous fluids or monitoring equipment can create a hazard for the patient and hospital personnel if allowed to dangle freely across the floor. In the interest of safety, various devices have been developed to organize the tubing.

Numerous innovations have been provided in prior art that are adapted to an enveloping assembly and method for securing medical wiring, cords and tubes. Even though these innovations may be suitable for the specific purposes to which they address, however, they would not be as suitable for the purposes of the present invention.

For example, U.S. Pat. No. 4,074,397 to Rosin discloses a disposable device is provided for securing cords and tubes extending to or from the patient may be conveniently fastened, wherein the device comprises a thin flexible pad having a pressure-sensitive adhesive layer on one side.

U.S. Pat. No. 4,336,806 to Eldridge, Jr. discloses a medical tube holder comprising a backing strip having tube receiving locations and magnetic materials to hold medical tubing which is often employed in surgical operations.

U.S. Pat. No. 4,639,980 to Peterson discloses a tubing organizer for hospital use having Velcro straps, a Teflon loop and a stainless steel clip connected by stainless steel eyelets.

U.S. Pat. No. 4,640,032 to Lewis discloses a wire and cable organizing sleeve for individually ordering a plurality of specified wires or cables of differing gauges and lengths to be secured between two spatially separated adjacent pairs of elongated strips.

U.S. Pat. No. 4,664,103 to Martin et al. and U.S. Pat. No. 5,010,899 to Thompson disclose a surgical drape comprising provisions to hold tubing, cords and the like that are employed during surgical operations.

U.S. Pat. No. 5,082,111 to Corbitt, Jr. et al. discloses a disposable surgical instrument holder for holding a number of surgical instruments, tubes and cords.

U.S. Pat. No. 5,464,025 to Charles et al. discloses a self-contained surgical tubing management system to incorporate surgical hand piece(s) and power and fluid tubing, cables and connections in pockets formed within a single disposable package. Further the tubing management system includes a sterile sheet or substrate that may cover either all or only a portion of the patient's body.

U.S. Pat. No. 5,535,787 to Howell discloses a flexible cable holder comprising a flexible web with a plurality of edge fasteners forming an enclosed duct for retaining cables, wires and power cords.

U.S. Pat. No. 5,624,403 to Jaquith discloses a management system for flexible lines, such as tubes and cables, used in the medical treatment of a patient includes a flexible expanse of material and a plurality of separate connectors mounted at different positions on the material. The connectors are separately operable for attaching and detaching respective lines independently of the attachment and detachment of other lines.

U.S. Pat. No. 5,709,665 to Vergano et al. discloses a disposable device and method for holding a plurality of medical conduits comprising an elongated foam strip having adhesive on a first surface of the strip. A clip is provide at the first end for releasably attaching the device to a bed sheet, blanket or patient's clothing, and the second end is folded over toward the first end with the conduits secured between the layers by the adhesive layer which substantially surrounds the circumference of each conduit to hold the same without allowing the conduits to be twisted or pulled through the holder.

U.S. Pat. No. 5,836,453 to Herrera discloses a pouch for organizing and suspending cables off of a hospital floor. The pouch comprises an envelope-like formation to enclose a plurality of cables.

U.S. Pat. No. 6,315,759 to Peterson discloses a protective cover comprising generally cylindrical hollow tube composed of a flexible, resilient material such as closed-cell foam, enabling the tube to be placed around and over the elongated member such as a plurality of intravenous lines, baby crib rails, bicycle frame sections, handles and other items.

It is apparent now that numerous innovations for an enveloping assembly and method for securing medical wiring, cords, and tubes have been developed in the prior art that are adequate for various purposes. Furthermore, even though these innovations may be suitable for the specific purposes to which they address, accordingly, they would not be suitable for the purposes of the present invention as heretofore described. Thus an enveloping assembly and method for sterilized and static resistant ordering of medical wiring and tubes that organizes electrical wires, cords, and tubes while maintaining a sterile environment for the electrical wires, tubes, and cords and preventing static electricity discharge from the electrical wiring is needed. Further often there is a need to be able to temporarily anchor such elongated surgical equipment. After being deposited, the elongated equipment must be easily retrievable for further use during the particular operation.

SUMMARY OF THE INVENTION

The present invention discloses a system and method for ordered holding of medical wiring and tubes, the system and method includes laying an outer panel over a medical environment, wherein the outer panel is defined by a flexible, sterilized nonwoven fabric; overlaying the outer panel with an inner panel, such that the inner panel remains within the edges of the outer panel, wherein the inner panel has electrical charge resistance property; positioning at least one elongated electrical member or at least one elongated tubular member or both on the inner panel; moving opposing edges of the inner panel in proximate relationship to one another and are secured by a securing mechanism, thereby forming a unitary sleeve to envelope the at least one elongated electrical member or the at least one elongated tubular member or the both; and fastening the unitary sleeve to the outer panel, wherein the fastener is configured to detachably attach to the top corner of the second edge of the inner panel.

In view of the foregoing, it is therefore an object of the present invention to provide an inexpensive, easy to use, and easy to manufacture cord holding assembly.

It is another object of the present invention to provide a holding assembly for sterilized and electric charge resistant ordering of medical wiring and tubes.

It is another object of the present invention to provide a holding assembly for medical wiring and tubes comprising an outer panel of sterilized nonwoven fabric, which is generally larger than an inner panel so as to protect the inner panel from contamination.

It is still another object of the present invention to provide a holding assembly for medical wiring and tubes comprising a removable clip for quick and easy detachable attachment of the holding assembly.

It is still another object of the present invention to provide a holding assembly for medical wiring and tubes comprising quick and easy formation of a unitary sleeve to envelope the medical wiring and tubes.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The invention will now be described, by way of example, with reference to the accompanying drawings, in which.

Like reference numerals refer to like parts throughout the various views of the drawings.

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Specific dimensions and other physical characteristics relating to the embodiments disclosed herein are therefore not to be considered as limiting, unless the claims expressly state otherwise.

An enveloping assembly 100 and method 300 for sterilized and static resistant ordering of medical wiring and tubes is referenced in FIGS. 1-5. The enveloping assembly 100 is configured to hold at least one elongated electrical member 200*a*, or at least one elongated tubular member 200*b*, or both for ordering. The enveloping assembly 100 utilizes a bundling style of ordering to prevent the elongated members from tangling or falling into a disorganized arrangement, especially near the area of a medical procedure.

The enveloping assembly 100 and method 300 enables sterilized and static resistant ordering of the elongated members, such as medical electrical wires, cords, and tubes. This creates a sterile environment for the wire and tubular elongated members 200*a* and 200*b*, while also preventing static electricity discharge from the various electrical wiring and circuitry. In one embodiment, the elongated wires and tubes 200*a* and 200*b* are operatively connected to surgical instruments used for medical procedures. The enveloping assembly 100 and method 300 enables sterilized and electrostatic resistant ordered holding of any type of elongated members as required without departing from the scope and spirit of the invention.

Figure 1:
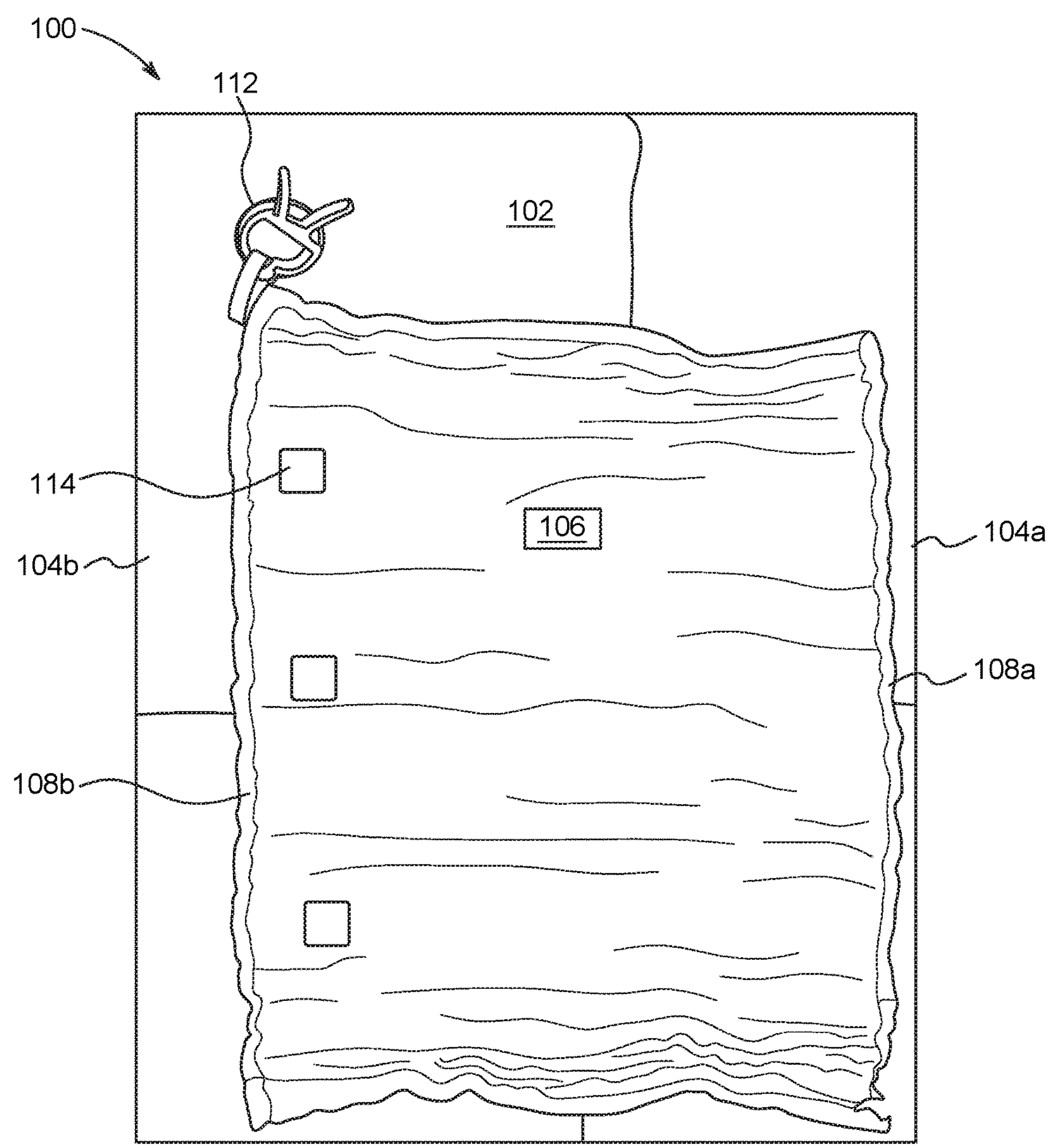
FIG. 1 illustrates a top view of an exemplary enveloping assembly and method for sterilized and static resistant ordering of medical wiring and tubes, showing an outer panel and an inner panel, in accordance with an embodiment of the present invention.

As referenced in FIG. 1, the enveloping assembly 100 comprises an outer panel 102 defined by a flexible, sterilized nonwoven fabric. The assembly 100 further comprises an inner panel 106 that overlays the outer panel 102. The inner panel 106 is disposed adjacent and coplanar to the outer panel 102, lying generally within the edges 104*a*, 104*b* of the outer panel 102.

In some embodiments, the inner panel 106 may receive the elongated members directly in an electrically neutralized electrostatic resistant environment. The inner panel 106 is generally made up of a heavy nonwoven drape, which is configured to be flexible and static charge resistant. The inner panel 106 enables enveloping of the elongated members while preventing static discharge between wires and panels 102 and 106. Simultaneously, the outer panel 102 made up of a flexible, sterilized nonwoven fabric, thereby the outer panel forms an outer barrier that helps to protect the inner panel 106 and the elongated members 200*a* and 200*b* against contamination by germs.

Figure 2:
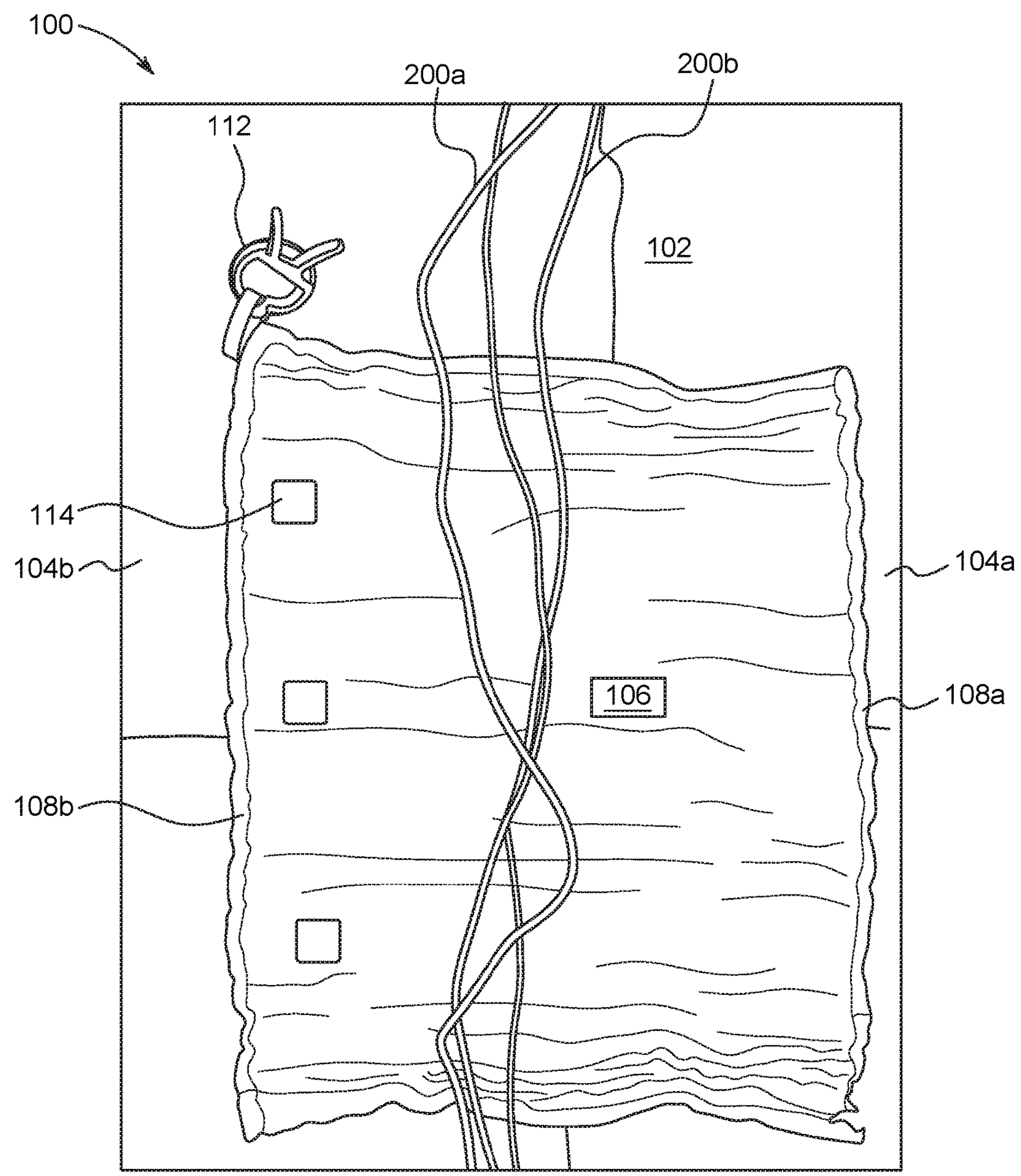
FIG. 2 illustrates a top view of the enveloping assembly shown in FIG. 1, showing elongated members on the inner panel, in accordance with an embodiment of the present invention.
Figure 3:
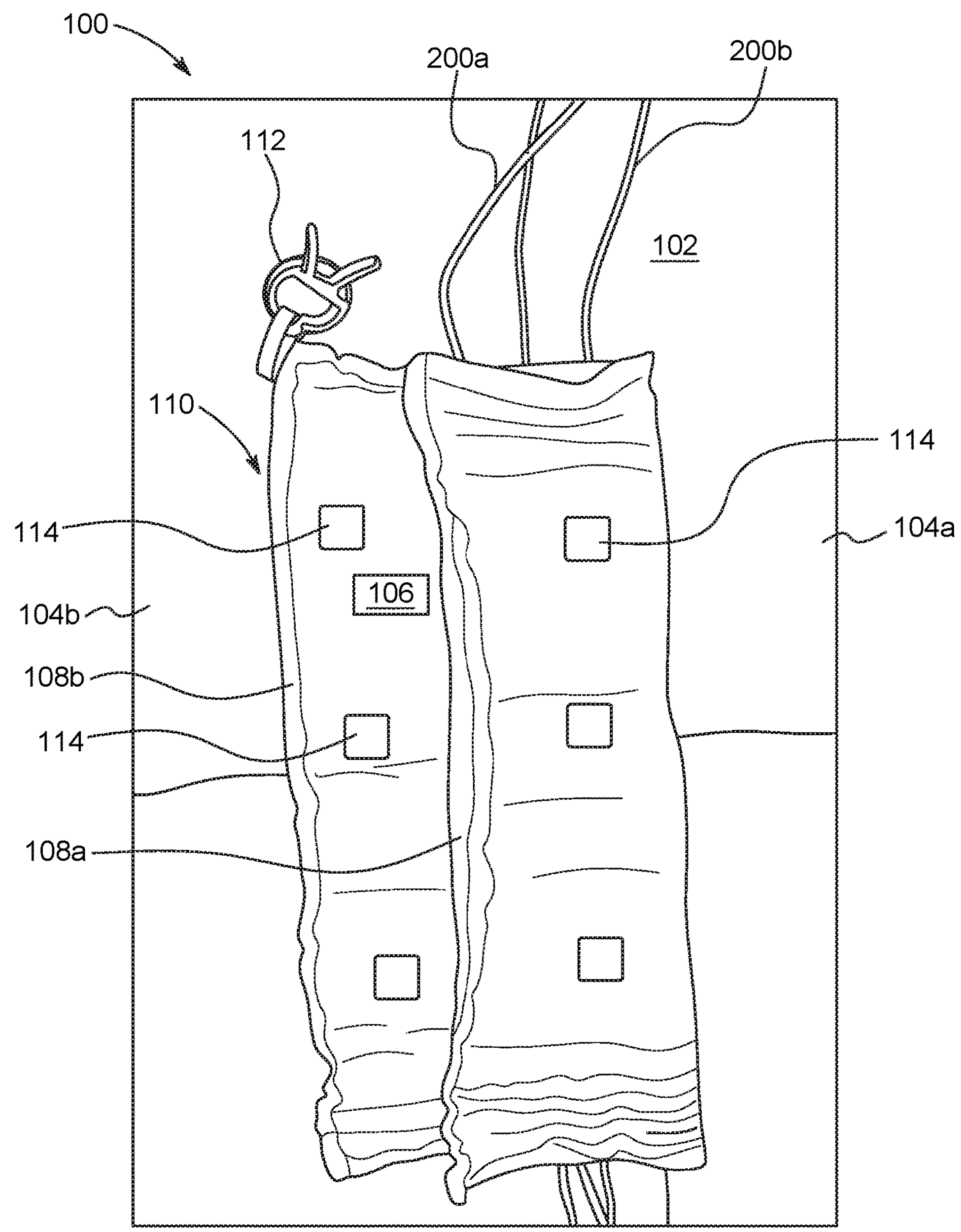
FIG. 3 illustrates a top view of the enveloping assembly shown in FIG. 1, showing elongated members on the inner panel and the inner panel partially folded, in accordance with an embodiment of the present invention.

As shown in FIG. 2, the outer panel 102 is generally larger than the inner panel 106 because the outer panel 102 must maintain sterilized segregation between contaminated environments, e.g., hospital, surgical room, and the sterilized environment in which the inner panel 106 and the elongated members reside.

Additionally, the outer panel 102 is configured to envelope the inner panel 106 and the elongated members to form a unitary sleeve 110. The unitary sleeve 110 is formed by moving opposing edges 108*a* and 108*b* of the inner panel 102 in proximate relationship to one another and are secured by a securing mechanism 114, thereby forming a unitary sleeve 110 to envelope the at least one elongated electrical member 200*a* or the at least one elongated tubular member 200*b* or the both 200*a* and 200*b*.

In an alternative embodiment of the present invention, the inner panel 106, being generally resilient, moves in conjunction with the outer panel 102. Thus by moving the corresponding opposing edges of the inner panel (108*a* and 108*b*) and the outer panel (104*a* and 104*b*) in proximate relationship to one another, so as to envelop the at least one elongated electrical member 200*a* or the at least one elongated tubular member 200*b* or the both 200*a* and 200*b* while the inner panel 106 not being exposed to the atmosphere, thereby preventing contamination.

In another embodiment, a fastener 112 joins with the outer panel 102, and fastens the unitary sleeve 110 close. The fastener 112 may also detachably attach to a mounting surface.

In one aspect of the present invention, a holding assembly 100 for ordered holding elongated members 200*a* and 200*b*, the assembly 100 comprising, an outer panel 102 defined by a flexible, sterilized nonwoven fabric configured to protect against contamination; an inner panel 106 disposed adjacent and coplanar to the outer panel 102, the inner panel 106 defined by a flexible, static charge resistant, nonwoven fabric, wherein a unitary sleeve 110 is formed from a first and a second opposing edges (108*a* and 108*b*) of the inner panel 106 being in proximate relationship to one another and are secured by a securing mechanism 114 so as to envelope at least one elongated member (200*a*, 200*b*); and a fastener 112 configured to detachably attach the unitary sleeve 110 to the outer panel 102.

In another aspect of the present invention, a holding assembly 100 for sterilized and static charge resistant ordering of medical wiring and tubes (200*a* and 200*b*), the assembly 100 comprising, an outer panel 102 defined by a flexible, sterilized nonwoven fabric configured to help protect against contamination; an inner panel 106 disposed adjacent and coplanar to the outer panel 102, the inner panel 106 defined by a flexible, static charge resistant, nonwoven fabric, the inner panel 106 configured to enable enveloping of at least one elongated electrical member 200*a*, or at least one elongated tubular member 200*b*, or both, wherein the enveloping configuration forms a unitary sleeve 110 from a first and a second opposing edges (108*a* and 108*b*) of the inner panel 106 being in proximate relationship to one another and are secure by a securing mechanism 114; and a fastener 112 configured to detachably attach to the top corner of the second edge 108*b* of the inner panel 106, wherein the fastener 112 further configured to removably fasten the unitary sleeve 110 to the outer panel 102.

In another aspect of the present invention, a method 300 for ordered holding of medical wiring 200*a* and tubes 200*b*, the method comprising, laying an outer panel over a medical environment 302, wherein the outer panel is defined by a flexible, sterilized nonwoven fabric; overlaying the outer panel with an inner panel, such that the inner panel remains within the edges of the outer panel 304, wherein the inner panel has electrical charge resistance property; positioning at least one elongated electrical member or at least one elongated tubular member or both on the inner panel 306; moving opposing edges of the inner panel in proximate relationship to one another and are secured by a securing mechanism, thereby forming a unitary sleeve to envelope the at least one elongated electrical member or the at least one elongated tubular member or the both 308; fastening the unitary sleeve to the outer panel, wherein the fastener is configured to detachably attach to the top corner of the second edge of the inner panel 310 and detachably mounting the outer panel to a mounting surface 312.

In another aspect of the present invention, an enveloping assembly 100 and method 300 for sterilized and static resistant ordering of medical wiring and tubes, comprises, an outer panel 102 defined by a flexible, sterilized, nonwoven fabric configured to help protect against contamination by germs; an inner panel 106 disposed adjacent and coplanar to the outer panel 102, the inner panel 106 defined by a flexible, static charge resistant, nonwoven fabric, the inner panel 106 configured to enable enveloping of at least one elongated electrical member 200*a*, or at least one elongated tubular member 200*b*, or both; whereby the outer panel 102 is configured to envelope the inner panel 106 and the elongated members 200*a*, 200*b* to form a unitary sleeve 110, whereby the unitary sleeve 110 is formed from opposing edges 104*a*, 104*b* of the outer panel 102 and opposing edges 108*a* and 108*b* of the inner panel 106 being in proximate relationship to one another; and a fastener 112 configured to join with the outer panel 102, the fastener 112 further configured to fasten the unitary sleeve 110, the fastener 112 further configured to enable detachable attachment to a mounting surface.

In another aspect, the outer panel 102 is generally larger than the inner panel 106.

In another aspect, the outer panel 102 has a generally flat, rectangular shape.

In another aspect, the outer panel 102 is sterile.

In another aspect, the inner panel 106 has a generally flat, rectangular shape.

In another aspect, the inner panel 106 is resilient.

In another aspect, the inner panel 106 comprises a heavy type of drape material.

In another aspect, the inner panel 106 has a high electrical resistance.

In another aspect, the fastener 110 is a clip.

In another aspect, the unitary sleeve 110 holding elongated members 200*a* and 200*b* mount over a sterile drape 102.

In another aspect, the outer panel 102 is made of anti-bacterial non-woven fabric.

In another aspect, the securing mechanism 114 comprises a hook and loop mechanism, wherein the other types of securing mechanism can be used without departing from the scope and spirit of the present invention.

In another aspect, a continuous strip of the hook and loop mechanism or small pieces of hook and loop mechanism 114 at regular intervals may be attached to the opposing edges (108*a* and 108*b*) of the inner panel 106 to facilitate fastening of the opposing edges (108*a* and 108*b*) to form the unitary sleeve 110.

One objective of the present invention is to prevent medical electrical and tubular elongated members (200*a* and 200*b*) from tangling or falling into a disorganized arrangement, especially near the area of a medical procedure.

Another objective is to maintain a sterilized environment for the inner panel 106 and the contained elongated members (200*a* and 200*b*) therein.

Yet another objective is to prevent static electrical discharge from the wiring while being contained in the unitary sleeve 110.

Yet another objective is to securely fasten the formed unitary sleeve 110 in a closed position.

Yet another objective is to quickly clip on and clip off the assembly 100 to a surgical drape.

Yet another objective is to provide inner and outer panels 102, 106 that are sterile, disposable, simple and quick to use, and inexpensive to fabricate.

Yet another objective is to enable hospitals to purchase the assembly 100 to add to their surgical, patient drape packs; or to sell to a company that makes surgical packs, for including the enveloping assembly 100 with their own surgical packs.

As discussed above, the assembly 100 is configured to hold at least one elongated electrical member 200*a*, or at least one elongated tubular member 200*b*, or both for ordering to prevent the elongated members from tangling or falling into a disorganized arrangement, especially near the area of a medical procedure. The enveloping assembly 100 provides sterilized and static resistant ordering of the elongated members 200*a*, 200*b*, such as medical electrical wires, cords, and tubes, while maintaining a sterile environment for the elongated members and preventing static electricity discharge from the electrical wiring.

Those skilled in the art will recognize that surgery require a multiplicity of electric wires, cables, and tubes to be inserted into the patient, or attached to electrodes on the patient. Problems have arisen in the past in providing adequate means for securing such wires, tubes, and cords so that they may be firmly held during the operation in positions in which they will not interfere with the medical professional performing a medical procedure. Desirably, the wires, tubes, and cords would be attached to the patient's body, or to drapes or covers shielding the patient's body, in order to minimize inconvenience to the medical professional.

Unfortunately, due to the uneven surfaces afforded by the patient's body, it has been impractical for such elongated members to be located any closer than a nearby surgical tray, or often lying in disarray at the feet of the medical professional. The present invention provides a unique enveloping assembly 100 that organizes the wires, tubes, and cords, while also maintaining a sterile environment for the wires, tubes, and cords and preventing static electricity discharge from electrical wiring.

As referenced in FIG. 1, the assembly 100 comprises an outer panel 102 defined by a flexible, sterilized, nonwoven fabric configured to help protect against contamination by germs. In one embodiment, the outer panel 102 is sterile. Though any sanitization means, e.g., ultraviolet light, disinfecting compositions, etc., may be used to ensure substantially complete sanitization of the outer panel 102.

The assembly 100 further comprises an inner panel 106 that works in conjunction with the outer panel 102. The inner panel 106 is disposed adjacent and coplanar to the outer panel 102, lying within the edges 104*a*, 104*b* of the outer panel 102. The inner panel 106 is configured to envelop the at least one elongated electrical member 200*a*, or the at least one elongated tubular member 200*b*, or both. Additionally the outer panel 102 may be wrapped over the inner panel 106 envelop configuration as the inner panel 106, similar to the outer panel 102, is sufficiently resilient to conform to the enveloping articulation of the outer panel 102.

In some embodiments, the inner panel 106 may be defined by a flexible, static charge resistant, nonwoven fabric. The inner panel 106 provides the resistance to electrostatic charges to protect short circuits when multiple wires are bundled together within the inner panel 106. In some embodiments, the fabric of the inner panel 106 is an electrostatic discharge material, such as a plastic that reduces static electricity to protect electrostatic-sensitive devices and wires. In another embodiment, the fabric of the inner panel 106 is an insulative material that prevents or limits the flow of electrons across the inner panel 106 surface or through the volume of the inner panel 106. This configuration of the inner panel 106 has a high electrical resistance and is difficult to ground.

The outer panel 102 is generally larger than the inner panel 106 because the outer panel 102 must maintain sterilized segregation between a contaminated environment, and the sterilized environment in which the inner panel 106 and the elongated members reside. In one embodiment shown in FIG. 2-4, the inner panel 106 contains the elongated members in a longitudinal disposition; the outer panel 102 contains the inner panel 106 and the elongated members; and the edges 108*a*, 108*b* of the inner panel 106 are brought together to envelop the elongated members 200*a*, 200*b* and are secured by a securing mechanism 114, thereby forming a unitary sleeve 110. The outer panel 102 being larger than the inner panel 106, thus envelop the entirety of the inner panel 106; thereby preventing contamination from germs, bacteria, body fluids, and other contaminates that may be found in a medical environment.

In some embodiments, the edges 104*a*, 104*b* of the outer panel 102 are brought together (not shown) to envelop the entirety of the inner panel 106 that is configured to the unitary sleeve 110; thereby preventing contamination from germs, bacteria, body fluids, and other contaminates that may be found in a medical environment.

Figure 4:
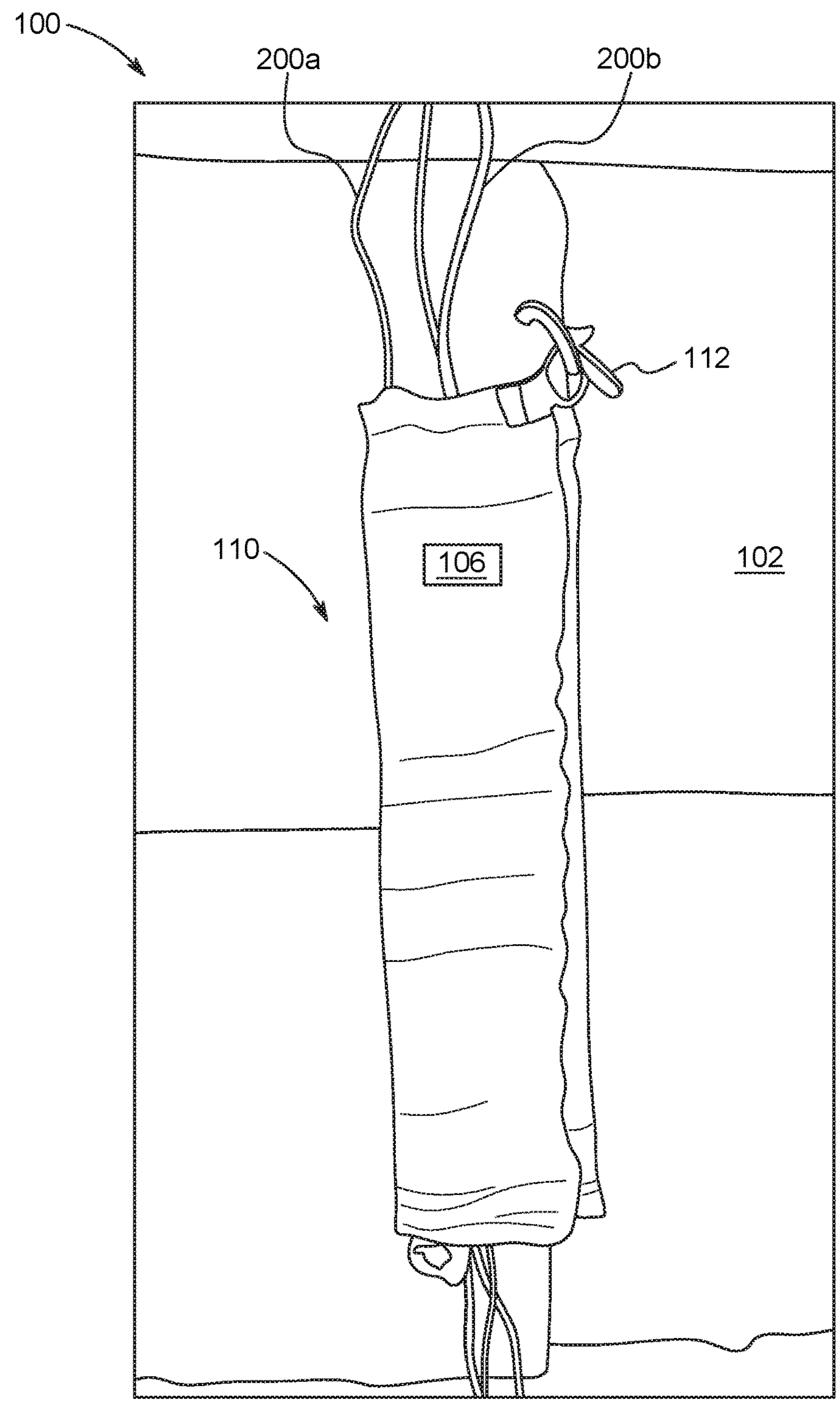
FIG. 4 illustrates a top view of the enveloping assembly, showing elongated members on the inner panel and the inner panel partially folded into a unitary sleeve, in accordance with an embodiment of the present invention.

Turning now to FIG. 4, the inner panel 106 is configured to envelope the elongated members 200*a*, 200*b* to form a unitary sleeve 110. The unitary sleeve 108 is easily formed by folding the second edge 108*b* over the first edge 108*a* of inner panel 106 to envelop the elongated members within the unitary sleeve 110. In essence, the unitary sleeve 110 is formed from opposing edges 108*a*, 108*b* of the inner panel 106 being in proximate relationship to one another and is secured by a securing mechanism 114. Further the outer panel 102 being a sterilized drape and larger than the unitary sleeve 110 can envelop the unitary sleeve completely thereby creating a sterilized envelope that segregates the inner panel 102 and the elongated members (200*a* and 200*b*) from the contaminated environment. Conversely, the elongated members 200*a*, 200*b* may be removed from the assembly 100 by separating the edges 108*a* and 108*b* of the inner panel 106 and removing the elongated members form the inner panel 106.

Looking back at FIG. 1, the assembly 100 comprises a fastener 112 configured to join with the outer panel 102. The fastener 112 helps fasten the unitary sleeve 110 in a closed position that maintains the device 100 protected from the environment. The fastener 112 is also effective for simultaneously detachably attaching to a mounting surface. In one embodiment, the fastener 112 is a clip, and the mounting surface is a surgical drape. Though any type of fastener, such as hook and loop fasteners, magnets, screws, and adhesives may be used without departing from the scope and spirit of the present invention.

Figure 5:
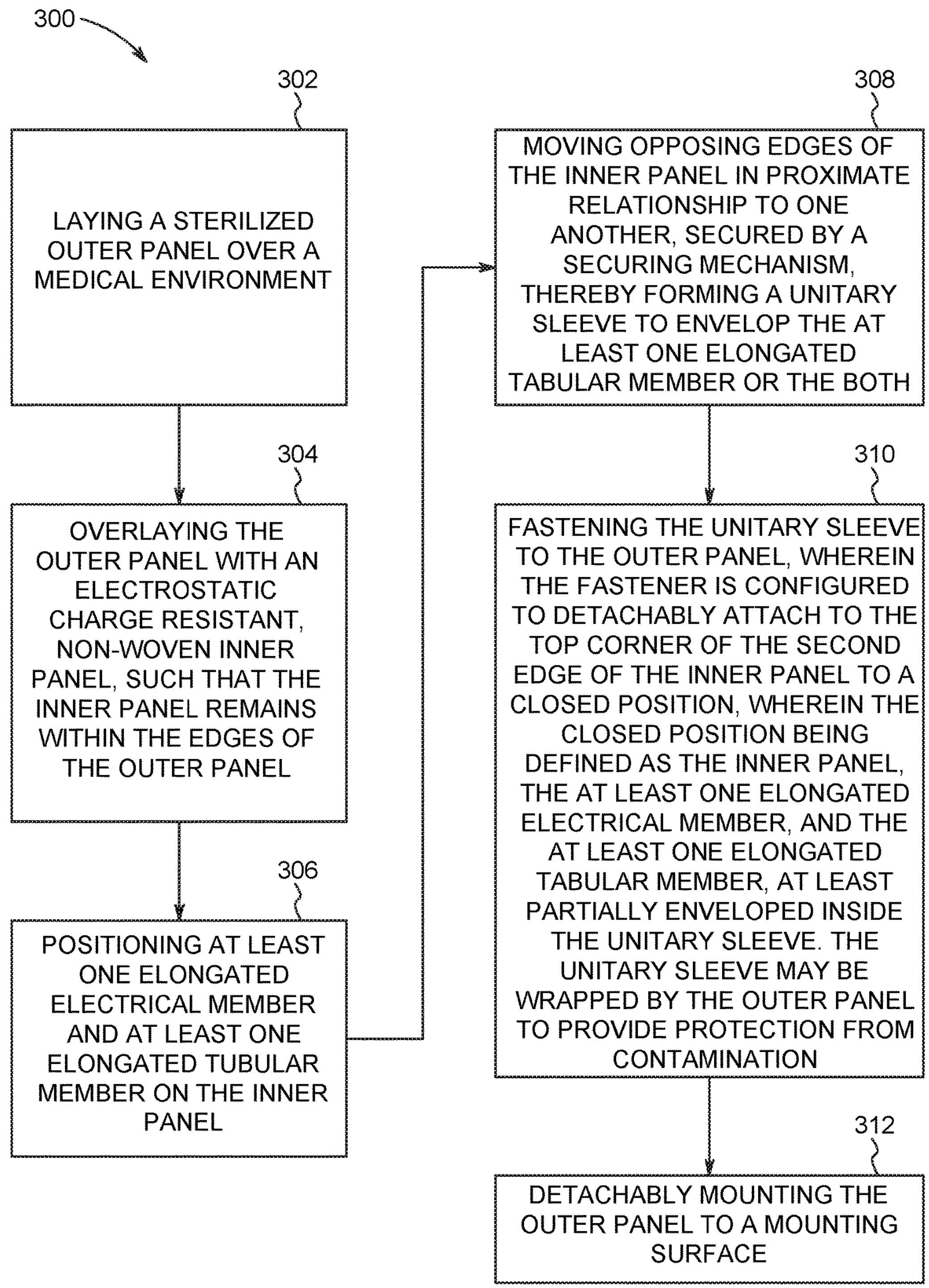
FIG. 5 illustrates a flowchart of an exemplary method for sterilized and static resistant ordering of medical wiring and tubes, in accordance with an embodiment of the present invention.

FIG. 5 illustrates a flowchart of an exemplary method 300 for sterilized and static resistant ordering of medical wiring and tubes. The method 300 comprises an initial Step 302 of laying an outer panel over a medical environment, wherein the outer panel defined by a flexible, sterilized nonwoven fabric configured to protect against contamination. A step 304 may include overlaying the outer panel with an inner panel, such that the inner panel remains within the edges of the outer panel. A step 306 further comprises positioning at least one elongated electrical member or at least one elongated tubular member or both on the inner panel, wherein the inner panel defined by a flexible, electrostatic charge resistant, nonwoven fabric. Then in a step 308 may include moving opposing edges of the inner panel in proximate relationship to one another and are secured by a securing mechanism, thereby forming a unitary sleeve to envelope the at least one elongated electrical member or the at least one elongated tubular member or the both. A step 310 includes fastening the unitary sleeve to the outer panel, wherein the fastener is configured to detachably attach to the top corner of the second edge of the inner panel to a closed position, wherein the closed position being defined as the inner panel, the at least one elongated electrical member, and the at least one elongated tubular member at least partially enveloped inside the unitary sleeve. A final step 312 comprises detachably mounting the outer panel to a mounting surface, wherein the mounting surface is a surgical drape or any surface at the medical environment around the patient.

In an alternative embodiment of the invention, the outer panel 102 is configured to envelope the inner panel 106 and the elongated members 200*a*, 200*b* to form a unitary sleeve. The unitary sleeve is easily formed by folding the outer panel 102 over to contain the inner panel 106 and the elongated members. In essence, the unitary sleeve can be formed from opposing edges 104*a*, 104*b* of the outer panel 102 being in proximate relationship to one another. This creates a sterilized envelope that segregates the contents of the outer panel 102 from the environment. Conversely, the elongated members 200*a*, 200*b* may be removed from the assembly 100 by separating the edges 104*a*, 104*b* of the outer panel 102 and removing the elongated members form the inner panel 102.

These and other advantages of the invention will be further understood and appreciated by those skilled in the art by reference to the following written specification, claims and appended drawings.

Because many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What is claimed is:

1. A holding assembly for ordered holding elongated members, the assembly comprising:

an outer panel defined by a flexible, sterilized nonwoven fabric configured to protect against contamination by being at least partially disposed over at least a portion of a medical environment to provide a germ barrier of flexible, sterilized nonwoven fabric over the at least a portion of said medical environment;

an inner panel configured to be overlaid over, adjacent, and coplanar to the outer panel while the outer panel is at least partially disposed over the at least a portion of said medical environment to provide the germ barrier of flexible, sterilized nonwoven fabric over the at least a portion of said medical environment, the inner panel defined by a flexible, static charge resistant, nonwoven fabric, wherein the inner panel is further configured to be formed into a unitary sleeve at least in part via first and second opposing edges of the inner panel being brought in proximate relationship to one another and being secured by a securing mechanism so as to envelope at least one elongated member; and a fastener configured to detachably attach the unitary sleeve to the outer panel, wherein the fastener includes only a clip and does not include either an adhesive material and a hook and loop fastener.

2. The assembly of claim 1, wherein the outer panel is at least one of generally larger than the inner panel or generally of a flat, rectangular shape.

3. The assembly of claim 1, wherein the inner panel has a generally flat, rectangular shape.

4. The assembly of claim 1, wherein the outer panel is made of antibacterial non-woven fabric.

5. The assembly of claim 1, wherein the inner panel has electrical charge resistance property.

6. The assembly of claim 1, wherein the elongated members comprise at least one elongated electrical member, or at least one elongated tubular member, or both.

7. The assembly of claim 1, wherein the clip is configured to detachably attach the outer panel to at least a mounting surface of the medical environment.

8. The assembly of claim 1, wherein the outer panel the first and second opposing edges of the outer panel and is configured to be wrapped to bring the first and second opposing edges of the outer panel in a proximate relationship to one another and wherein the inner panel is configured to form the unitary sleeve when the inner panel is overlaid over, adjacent and coplanar to the outer panel and the inner panel is moved in conjunction with the wrapping of the outer panel.

9. A holding assembly for sterilized and static charge resistant ordering of medical wiring and tubes, the assembly comprising:

an outer panel defined by a flexible, sterilized nonwoven fabric configured to help protect against contamination by being at least partially disposed over at least a portion of a medical environment to provide a germ barrier of flexible, sterilized nonwoven fabric over the at least a portion of said medical environment;

an inner panel configured to be overlaid over, adjacent, and coplanar to the outer panel while the outer panel is at least partially disposed over the at least a portion of said medical environment to provide the germ barrier of flexible, sterilized nonwoven fabric over the at least a portion of said medical environment, the inner panel defined by a flexible, static charge resistant, nonwoven fabric, the inner panel configured to enable enveloping of at least one elongated electrical member, or at least one elongated tubular member, or both, wherein the enveloping configuration forms a unitary sleeve from a first and a second opposing edges of the inner panel being in proximate relationship to one another and being secured by a securing mechanism; and a fastener configured to detachably attach to the top corner of the second edge of the inner panel, wherein the fastener further configured to removably fasten the unitary sleeve to the outer panel and wherein the fastener includes only a clip and does not include either an adhesive material and a hook and loop fastener.

10. The assembly of claim 9, wherein the outer panel is generally larger than the inner panel.

11. The assembly of claim 9, wherein the outer panel and the inner panel has a generally flat, rectangular shape.

12. The assembly of claim 9, wherein the inner panel has electrical charge resistance property.

13. The assembly of claim 9, wherein the outer panel being larger than the inner panel can create a sterilized envelope to the unitary sleeve and the at least one elongated electrical member, or the at least one elongated tubular member, or the both enveloped within the unitary sleeve.

14. The assembly of claim 9, wherein the the clip is configured to detachably attach the outer panel to at least a mounting surface of the medical environment.

15. A method for ordered holding of medical wiring and tubes, the method comprising:

laying at least a portion of an outer panel over at least a portion of a medical environment, the outer panel being defined by a flexible, sterilized nonwoven fabric, wherein the laying of the at least a portion of the outer panel over the at least a portion of said medical environment provides a germ barrier of flexible, sterilized nonwoven fabric over the at least a portion of said medical environment;

overlaying the outer panel with an inner panel while the at least a portion of the outer panel is laid over the at least a portion of the medical environment providing the germ barrier of flexible, sterilized nonwoven fabric over the at least a portion of said medical environment, such that the inner panel remains within the edges of the outer panel, wherein the inner panel has electrical charge resistance property;

positioning at least one elongated electrical member or at least one elongated tubular member or both on the inner panel;

moving opposing edges of the inner panel in proximate relationship to one another and securing the opposing edges of the inner panel with a securing mechanism, thereby forming a unitary sleeve to envelope the at least one elongated electrical member or the at least one elongated tubular member or the both;

fastening the unitary sleeve to the outer panel with a fastener, wherein the fastener is configured to detachably attach to the top corner of the second edge of the inner panel and wherein the fastener includes only a clip and does not include either an adhesive material and a hook and loop fastener; and detachably mounting the outer panel to a mounting surface.

16. The method of claim 15, wherein laying an outer panel includes at least laying an outer panel that is at least generally larger than the inner panel so as to protect the inner panel from contamination.

17. The method of claim 15, wherein fastening the unitary sleeve to the outer panel includes at least fastening the unitary sleeve to the outer panel with a fastener that is only a clip and wherein clip is configured to detachably attach the outer panel to at least a mounting surface of the medical environment.

* * * * *